United States Patent [19]
Pfister et al.

[11] Patent Number: 5,436,264
[45] Date of Patent: Jul. 25, 1995

[54] N-ARYLOXYALKYL TRYPTAMINE $\alpha_1$-ADRENERGIC RECEPTOR ANTAGONISTS

[75] Inventors: Jurg R. Pfister, Los Altos; David E. Clarke, Mountain View, both of Calif.

[73] Assignee: Syntex (U.S.A.) Inc., Palo Alto, Calif.

[21] Appl. No.: 109,294

[22] Filed: Aug. 19, 1993

[51] Int. Cl.$^6$ .................. A61K 31/40; C07D 209/14; C07D 405/12
[52] U.S. Cl. .................. 514/415; 514/414; 514/419; 548/467; 548/486; 548/492; 548/507
[58] Field of Search .......... 514/414, 419, 415; 548/467, 486, 492, 507

[56] References Cited

U.S. PATENT DOCUMENTS 3,371,098 2/1968 Kralt et al. ...................... 548/507
4,404,217 9/1983 Demarne et al. ............... 548/507 X

OTHER PUBLICATIONS

Protiva, M.; Vejdelek, Z. J.; Rajsner, M.; *Collection Czechoslov. Chem. Commun.* (1963) 28: 629.

*Primary Examiner*—Jacqueline Haley
*Attorney, Agent, or Firm*—Wayne W. Montgomery

[57] ABSTRACT

The present invention relates to novel N-aryloxyalkyl tryptamine $\alpha_1$-adrenergic receptor antagonists of the formula I:

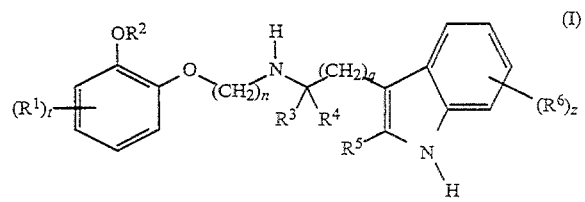

in which n is 2, 3 or 4; q is 1, 2 or 3; t is 0, 1, 2 or 3; z is 0, 1, 2 or 3; each $R^1$ and $R^2$ are independently hydroxy, halogen, cyano, $(C_{1-8})$alkyl, $(C_{1-8})$alkyloxy or trifluoromethyl; and $R^2$ is hydrogen, $(C_{1-4})$alkyl, fluoro$(C_{1-4})$alkyl, difluoro$(C_{1-4})$alkyl, trifluoro$(C_{1-4})$alkyl, $(C_{1-4})$alkyloxy$(C_{1-4})$alkyl, oxo$(C_{1-4})$alkyl, $(C_{1-8})$cycloalkyl, $(C_{1-8})$cycloalkylmethyl or allyl or phenyl$(C_{1-4})$alkyl or heterocyclo$(C_{1-8})$alkyl (optionally substituted with one to two substituents independently selected from $(C_{1-4})$alkyl, $(C_{1-4})$alkyloxy, trifluoromethyl and halogen); $R^3$ and $R^4$ are independently hydrogen, $(C_{1-4})$alkyl, $(C_{1-8})$cycloalkyl, $(C_{1-8})$cycloalkylmethyl or allyl; and $R^5$ is hydrogen, $(C_{1-4})$alkyl, $(C_{1-8})$cycloalkyl, $(C_{1-8})$cycloalkylmethyl, allyl, $(C_{1-4})$alkylsulfonyl and aminocarbonyl; with the proviso that when n is 2, t is 0, q is 1, z is 0, 1 or 2, $R^5$ is hydrogen and $R^6$ is hydroxy or $(C_{1-8})$alkyloxy then at least one of $R^3$ and $R^4$ is not hydrogen; and the pharmaceutically acceptable salts, individual isomers, and mixtures of isomers thereof; their uses as therapeutic agents and the methods of their making.

16 Claims, No Drawings

N-ARYLOXYALKYL TRYPTAMINE $\alpha_1$-ADRENERGIC RECEPTOR ANTAGONISTS

FIELD OF THE INVENTION

This invention relates to novel N-aryloxyalkyl tryptamine $\alpha_1$-adrenergic receptor antagonists, their uses as therapeutic agents, and the methods of their making.

BACKGROUND OF THE INVENTION

Alterations in $\alpha_1$-adrenergic receptors have far reaching physiological effects and drugs which selectively interact with $\alpha_1$-adrenergic receptors have an array of therapeutic applications. For example, $\alpha_1$-adrenergic receptor antagonists are useful in treating various cardiovascular disorders. $\alpha_1$-Adrenergic receptor antagonists block $\alpha$ receptors that mediate vasoconstriction in resistance arterioles and are useful as antihypertensive agents or as afterload reducing agents in treating congestive heart failure. Certain $\alpha_1$-adrenergic receptor antagonists can selectively reduce vascular resistance in specific organs (Blue, D.; Vimont, R.; Clarke, D. *Br. J. Pharmacol.* 1992, 107, 414-417) and are useful in treating ischemia of vital organs caused by, or associated with, persistent hypovolemic or cardiogenic shock or diabetic nephropathy. In addition, $\alpha_1$-adrenergic receptor stimulation contributes to arrhythmogenesis in the ischemic heart (Kurz, T.; Yamada, A.; DaTorre, S.; Corr, P. *Eur. Heart J.* 1991, 12, 88-98); thus, $\alpha_1$-adrenergic receptor antagonists are useful as antiarrhythmic agents.

$\alpha_1$-Adrenergic receptor antagonists are useful in treating various urinary tract disorders (Lepor, H. *The Prostate Supplement.* 1990, 3, 75-84). $\alpha_1$-Adrenergic receptor antagonists can selectively inhibit $\alpha_1$ receptor mediated contraction of urethral and bladder neck smooth muscle, leading to decreased resistance in urinary outflow, and are useful in treating urinary tract obstruction due to benign prostatic obstruction or any diseases which relate directly or indirectly to dysfunction of urinary smooth muscle or its innervation.

Stimulation of central nervous system $\alpha_1$-adrenergic receptors suppresses appetite (Wellman, P.; Davies, B. *Pharmacol. Biochem. Behav.* 1991, 42, 97-100); thus, $\alpha_1$-adrenergic receptor antagonists are useful in treating anorexia.

The disclosures of these and other documents referred to throughout this application (e.g., in the Pharmacology section of the Detailed Description of the Invention) are incorporated herein by reference.

SUMMARY OF THE INVENTION

The first aspect of this invention a compound of Formula I:

in which
n is 2, 3 or 4;
q is 1, 2 or 3;
t is 0, 1, 2 or 3;
z is 0, 1, 2 or 3; each
$R^1$ and $R^6$ are independently hydroxy, halogen, cyano, $(C_{1-8})$alkyl, $(C_{1-8})$alkyloxy or trifluoromethyl; and
$R^2$ is hydrogen, $(C_{1-4})$alkyl, fluoro$(C_{1-4})$alkyl, difluoro$(C_{1-4})$alkyl, trifluoro$(C_{1-4})$alkyl, $(C_{1-4})$alkyloxy$(C_{1-4})$alkyl, oxo$(C_{1-4})$alkyl, $(C_{1-8})$cycloalkyl, $(C_{1-8})$cycloalkylmethyl or allyl or phenyl$(C_{1-4})$alkyl or heterocyclo$(C_{1-4})$alkyl (optionally substituted with one to two substituents independently selected from $(C_{1-4})$alkyl, $(C_{1-4})$alkyloxy, trifluoromethyl and halogen);
$R^3$ and $R^4$ are independently hydrogen, $(C_{1-4})$alkyl, $(C_{1-8})$cycloalkyl, $(C_{1-8})$cycloalkylmethyl or allyl; and
$R^5$ is hydrogen, $(C_{1-4})$alkyl, $(C_{1-8})$cycloalkyl, $(C_{1-8})$cycloalkylmethyl, allyl, $(C_{1-4})$alkylsulfonyl and aminocarbonyl; with the proviso that when n is 2, t is 0, q is 1, z is 0, 1 or 2, $R^5$ is hydrogen and $R^6$ is hydroxy or $(C_{1-8})$alkyloxy then at least one of $R^3$ and $R^4$ is not hydrogen; and the pharmaceutically acceptable salts, individual isomers, and mixtures of isomers thereof.

A second aspect of this invention is a pharmaceutical composition which contains a compound of Formula I in admixture with one or more suitable excipients.

A third aspect of this invention is a method for treating a condition capable of amelioration by blocking $\alpha_1$-adrenergic receptors in an animal in need thereof, which method comprises administering to such animal a therapeutically effective amount of a compound of Formula I, or of an individual isomer, mixture of isomers, or the pharmaceutically acceptable salt or salts thereof.

A fourth aspect of this invention is the processes for preparing compounds of Formula I and is set forth in "Detailed Description of the Invention".

DETAILED DESCRIPTION OF THE INVENTION

Definitions:
Unless otherwise stated, the following terms used in the specification and claims have the meanings given below:

"Alkyl" means a straight or branched saturated hydrocarbon radical having from one to the number of carbon atoms designated (e.g., $(C_{1-4})$alkyl includes the radicals methyl, ethyl, prop-1-yl, prop-2-yl, but-1-yl, but-2-yl, 2-methylpropyl and 1,1-dimethylethyl).

"Alkenyl" means a straight or branched unsaturated hydrocarbon radical having from 3 to the number of carbon atoms designated and in which the carbon atom with the free valence is saturated (e.g., $(C_{3-4})$alkenyl includes the radicals 2-propenyl, 2-butenyl, 3-butenyl, 1-methyl-2-propenyl and 2-methyl-2-propenyl).

"Alkyloxy" means the radical —OR wherein R is alkyl having from one to the number of carbon atoms designated (e.g., $(C_{1-4})$alkyloxy includes the radicals methyloxy, ethyloxy, prop-1-yloxy, prop-2-yloxy, but-1-yloxy, but-2-yloxy, 2-methylprop-1-yloxy and 2-methylprop-2-yloxy).

"Halogen" means fluorine, chlorine, bromine, or iodine.

"Leaving group" has the meaning conventionally associated with it in synthetic organic chemistry, i.e., an atom or group displaceable under alkylating conditions, and includes halogen and alkane- or arenesulfonyloxy, such as mesyloxy, ethanesulfonyloxy, benzenesulfonyloxy and tosyloxy, and thienyloxy, dihalophosphinoyloxy, tetrahalophosphaoxy, and the like.

"Protective group" has the meaning conventionally associated with it in synthetic organic chemistry, i.e., a group which selectively blocks one reactive site in a multifunctional compound such that a chemical reaction can be carried out selectively at another unprotected reactive site and which can be readily removed after the selective reaction is completed. Certain processes of this invention rely upon protective groups to block reactive oxygen atoms present in the reactants (i.e., in the preparation of compounds of Formula I in which $R^1$ or $R^6$ is hydroxy or $R^2$ is hydrogen). Acceptable oxygen protective groups include substituted methyl and ethyl ethers and silyl ethers. For example, reactive oxygen atoms can be conveniently protected with a diphenylmethyl group, which is then conveniently removed after the selective reaction is completed by catalytic or chemical reduction.

"Animal" includes humans, non-human mammals, e.g., dogs, cats, rabbits, cattle, horses, sheep, goats, swine, and deer, and non-mammals, e.g., birds and the like.

"Disease" specifically includes any unhealthy condition of an animal or part thereof and includes an unhealthy condition which may be caused by, or incident to, medical or veterinary therapy applied to that animal, i.e., the "side effects" of such therapy.

"Optional" or "optionally" means that the subsequently described event or circumstance may or may not occur, and that the description includes instances where the event or circumstance occurs and instances in which it does not. For example, "optionally converting a compound of Formula I to a corresponding pharmaceutically acceptable salt" means that the conversion may or may not be carried out in order for the process described to fall within the invention, and the invention includes those processes wherein the compound of Formula I is converted to the salt and those processes in which it is not.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to effect such treatment for the disease.

The term "q.s." means adding a quantity sufficient to achieve a stated function, e.g., to bring a solution to the desired volume (i.e., 100%).

"Treating" or "treatment" of a disease includes:

(1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

The compounds of Formula I are named in accordance with acceptable nomenclature rules generally consistent with "Chemical Abstracts". For example, the compound of Formula I in which n is 2, p is 0, q is 1, z is 0, $R^5$ is hydrogen, and $R^3$ and $R^4$ are each methyl, i.e., of the structure

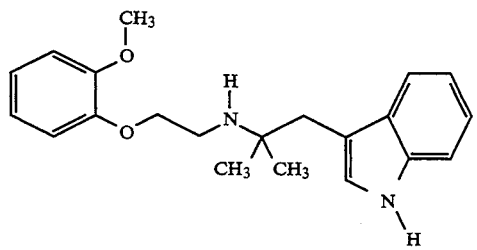

is named [2-(1H-indol-3-yl)-1,1-dimethylethyl][2-(2-methyloxyphenoxy)-ethyl]amine.

Presently Preferred Embodiments:

While the broadest definition of this invention is set forth in the Summary of the Invention, certain compounds of Formula I are preferred. For example, preferred compounds of Formula I are those in which n is 2, q is 1, z is 0 or 1, $R^2$ is $(C_{1-4})$alkyl, $(C_{1-8})$cycloalkylmethyl, allyl or phenyl$(C_{1-4})$alkyl, $R^3$ is $(C_{1-4})$alkyl, $R^5$ is hydrogen or $(C_{1-4})$alkyl, and $R^5$, when present, is hydroxy or halogen.

Particularly preferred compounds are those in which t is 0, n is 2, q is 1, z is 0 or 1, $R^2$ is $(C_{1-4})$alkyl or $(C_{1-8})$-cycloalkylmethyl, $R^3$ is $(C_{1-4})$alkyl, $R^5$ is hydrogen or methyl, and $R^6$, when present, is hydroxy, chloro or fluoro.

Pharmacology and Utility:

The compounds of this invention are $\alpha_1$-adrenergic receptor antagonists. The $\alpha_1$-adrenergic receptor affinity of test compounds can be determined by an in vitro, receptor binding assay which utilizes a membrane preparation isolated from rat submaxillary gland. The $\alpha_1$-adrenergic receptor affinity of test compounds can also be identified by an in vitro, receptor binding assay which utilizes a membrane preparation isolated from rat liver. The rat submaxillary gland and liver membrane receptor binding assays are both well established models for measuring the affinity of compounds for $\alpha_1$-adrenergic receptors (e.g., see Michel, A. D.; Loury, D. N.; Whiting, R. L. *Br. J. Pharmacol.* 1989, 98, 883–889) and are described in Example 5.

The antagonist properties of test compounds can be identified by an in vitro, functional assay which utilizes rat, isolated aortic smooth muscle and an $\alpha_1$-adrenergic receptor mediated contraction thereof (i.e., test compounds which inhibit agonist-induced, $\alpha_1$-adrenergic receptor mediated contractile responses are characterized as $\alpha_1$-adrenergic receptor antagonists). Antagonist properties of test compounds can also be identified by an in vitro, functional assay which utilizes rat, isolated perfused kidney and an $\alpha_1$-adrenergic receptor mediated increase in perfusion pressure (i.e., test compounds which inhibit agonist-induced, $\alpha_1$-adrenergic receptor mediated pressor responses are characterized as $\alpha_1$-adrenergic receptor antagonists. The rat, isolated aortic smooth muscle and the rat, isolated perfused kidney assays are both well established models for identifying and characterizing compounds that interact with $\alpha_1$-adrenergic receptors (e.g., see Hamed, A. T.; Johnson, T. D.; Charlton, K. G.; Clarke, D. E. *J. Autonom. Pharmacol.* 1983, 3, 265–273 and Blue, D. R.; Clarke, D. E. *Gen. Pharmacol.*, 1992, 23, 815–821, respectively) and are described in Examples 6 and 7, respectively.

As $\alpha_1$-adrenergic receptor antagonists, the compounds of this invention are useful for treating conditions which can be ameliorated by blocking $\alpha_1$-adrenergic receptors. Such conditions include anorexia, cardiovascular disorders, and urinary tract disorders. In addition, the compounds of this invention are useful for treating conditions associated with elevated intraocular pressure, particularly the elevated intraocular pressure associated with glaucoma.

Anorexia treatable with the compounds of this invention specifically include that which is caused by or associated with chronic conditions resulting in general wasting and malnutrition (e.g., cachexia induced by chronic anorexia nervosa, neoplasia, severe pain, severe congestive heart failure, respiratory failure, uremia, etc.), various endocrinopathies (e.g., hyperparathyroidism, Addison's disease, panhypopituitarism, etc.), therapeutic agents or procedures (e.g., antihypertensives, diuretics, digitalis, narcotic analgesics, chemotherapeutic agents, radiotherapy, etc.), or psychogenic disturbances (e.g., anxiety, depression, boredom, etc.).

Cardiovascular disorders treatable with the compounds of this invention include hypertension, congestive heart failure, variant angina due to coronary vasospasms, diseases which relate directly or indirectly to cardiac arrhythmias, and ischemia in vital organs (e.g., renal, cerebral and myocardial). Urinary tract disorders treatable with the compounds of this invention include diseases which relate directly or indirectly to dysfunction of the urinary tract (e.g., obstructive uropathies such as benign prostatic hypertrophy, prostatic carcinoma, chronic prostatitis, etc.) or diseases related to dysfunction of urinary smooth muscle or innervation.

Administration and Pharmaceutical Composition:

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from approximately 1.0 nanogram per kg (ng/kg) body weight per day to 1.0 mg/kg body weight per day. Preferably the amount will be approximately 10 ng/kg/day to 0.1 mg/kg/day. Therefore, a therapeutically effective amount for a 70 kg human may range from 70 ng/day to 70 mg/day, preferably 700 ng/day to 7.0 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of Formula I will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of Formula I in aerosol form. Inert gases suitable for this purpose are nitrogen, carbon dioxide, nitrous oxide, etc. Other suitable pharmaceutical carriers and their formulations are described in A. R. Alfonso *Remington's Pharmaceutical Sciences* 1985, 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise from 0.000001% w to 10.0% w of the compound of Formula I, preferably 0.00001%w to 1.0% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 4.

Processes for Preparing Compounds of the Invention:

The compounds of Formula I

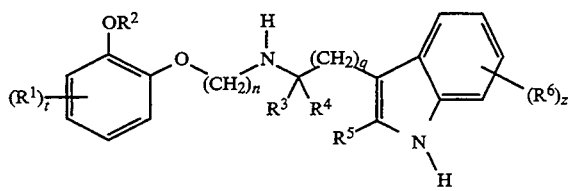

in which each n, q, t, z, $R^1$, $R^2$, $R^3$, $R^4$, $R^5$ and $R^6$ are as defined in the Summary of the Invention, can be prepared by a process which comprises reacting a compound of Formula II

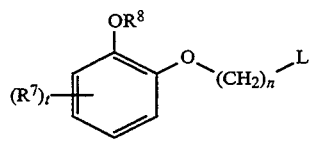

in which L is a leaving group; $R^7$ is not hydroxy but otherwise has the meaning of $R^1$ or is —$OR^9$, in which $R^9$ is a protective group; $R^8$ is not hydrogen but otherwise has the meaning of $R^2$ or is a protective group; and n and t are as defined above, with a compound of Formula III

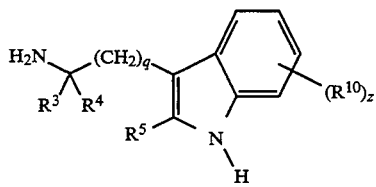

in which $R^{10}$ is not hydroxy but otherwise has the meaning of $R^6$ or is —$OR^9$, in which $R^9$ is a protective group, and each q, $R^3$, $R^4$ and $R^5$ are as defined above; and then when necessary removing any protective groups.

The reaction is carried out in the presence of base at 80° to 150° C. Suitable bases include potassium carbonate, sodium carbonate, triethylamine, etc., preferably potassium carbonate. Suitable solvents for the reaction include N,N-dimethylformamide (DMF), N-methylpyrrolidone, dimethylsulfoxide, etc., preferably DMF. The preparation of a compound of Formula I by the above process is described in Example 3.

The compounds of Formula II can be prepared by alkylation of an appropriate 2-hydroxy-1-[ω-hydroxy($C_{2-4}$)alkyloxy]benzene with a compound of the formula X—$R^7$, in which X is a leaving group and $R^7$ is as defined above, and then creating an appropriate leaving group L. The alkylation can be carried out in the presence of a base at 20° to 150° C. Suitable bases include potassium carbonate, sodium carbonate, etc., preferably potassium carbonate. Suitable solvents for the alkylation include acetone, (DMF), tetrahydrofuran (THF), etc., preferably DMF.

An appropriate leaving group L can be created by treatment with agents such as methanesulfonyl chloride, thionylchloride, phosphorous pentachloride, phosphorous oxychloride, and the like. Suitable solvents for the treatment include methylene chloride, chloroform, THF, etc., preferably methylene chloride. The preparation of a compound of Formula II is described in Example 1. A process for preparing 2-hydroxy-1-[ω-hydroxy($C_{2-4}$)alkyloxy]benzene derivatives is described in Bull. Chem. Soc. Japan. 1988, 61, 2050.

The compounds of Formula III in which q is 1 and one of $R^3$ and $R^4$ is hydrogen can be prepared either by reduction of an appropriate 3-(2-nitrovinyl)-1H-indole or by reduction of an appropriate 3-(2-nitroethyl)-1H-indole (Heath-Brown B.; Philpott, B. *J. Chem. Soc.* 1965, 7165). Compounds of Formula III in which q is 1 and both $R^3$ and $R^4$ are not hydrogen can be prepared by the latter method only.

Reduction of the 3-(2-nitrovinyl)indoles can be carried out with lithium aluminum hydride in THF. Appropriate 3-(2-nitrovinyl)indoles can be prepared by condensation of the corresponding indol-3-ylaldehyde with a nitro compound of the formula $R^3CH_2NO_2$, in which $R^3$ is as defined in the Summary of the Invention. Appropriate indol-3-ylaldehydes can be prepared by reaction of the corresponding 1H-indole with DMF and phosphorous oxychloride.

Suitable reducing agents for reduction of the 3-(2-nitroethyl)indoles include RANEY NICKEL® catalyst/hydrazine, hydrogen/palladium, sodium/ethanol, etc., preferably RANEY NICKEL® catalyst/hydrazine. Suitable solvents for the reduction include ethanol, methanol, THF, and the like. The preparation of a compound of Formula III by reduction of a 3-(2-nitroethyl)-1H-indole is described in Example 2, Step (c).

Appropriate 3-(2-nitroethyl)indoles can be prepared by reaction of the corresponding 3-(dimethylaminomethyl)-1H-indole with a molar excess of a nitro compound of the formula $R^3R^4CHNO_2$, in which $R^3$ and $R^4$ are as defined in the Summary of the Invention (with the proviso that at least one of $R^3$ and $R^4$ is not hydrogen), in the presence of base and at 60° to 150° C., and then acidifying. Suitable bases include sodium hydroxide, potassium hydroxide, calcium hydroxide, and the like. The preparation of an appropriate 3-(2-nitroethyl)-1H-indole is described in Example 2, Step (b).

Appropriate 3-(dimethylaminomethyl)indoles can be prepared by reaction of the corresponding 1H-indole with dimethylamine and formaldehyde in a suitable solvent at 0° to 75° C. Suitable solvents for the reaction include a 50/50 mixture of dioxane and 100% acetic acid, ethanol and acetic acid, THF and acetic acid, and the like. The preparation of an appropriate 3-(dimethylamino-methyl)-1H-indole is described in Example 2, Step (a).

Appropriate 3-(dimethylaminomethyl)indoles can also be prepared by reduction and attendant ring closure of the corresponding N,N-dimethyl-2-amino-α-phenyl-α-cyanoacetamide (Germain, C.; Bourdais, J. *J. Het. Chem.* 1976, 13, 1209). Appropriate α-nitroacetamides can be prepared by reduction of the corresponding N,N-dimethyl-2-cyano-α-phenyl-α-cyanoacetamide. Appropriate α-cyanoacetamides can be prepared by reaction of the corresponding 2-halo-1-nitrobenzene with 2-cyano-N,N-dimethylacetamide.

The compounds of Formula III in which q is 1 and both $R^3$ and $R^4$ are hydrogen can be prepared by reduction of an appropriate 3-cyanomethyl-1H-indole. The reduction can be carried out by refluxing with sodium in ethanol. Appropriate 3-cyanomethylindoles can be prepared by reaction of the corresponding 3-(dimethylaminomethyl)-1H-indole with sodium cyanide under nitrogen in ethylene glycol. Appropriate 3-(dimethylaminomethyl)indoles can be prepared as described above.

Other compounds of Formula III in which q is 1, 2 or 3 are either commercially available or can be readily prepared by application of the Fischer indole ring closure (Jackson, R.; Manske, R. *J. Amer. Chem. Soc.* 1930, 52, 5029) to a phenylhydrazone derivative of the following formula

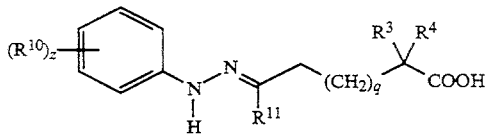

in which $R^{11}$ has the meaning of $R^5$ or is ethyloxycarbonyl and each q, z, $R^3$, $R^4$ and $R^{10}$ are as defined above. The indole ring closure and attendant esterification can be effected by heating the hydrazone in ethanol with sulfuric acid to produce an ethyl indol-3-yl-($C_{3-5}$) alkanoic acid ester. Hydrolysis of the ester produces the corresponding indol-3-yl($C_{3-5}$)alkanoic acid. When $R^{11}$ is ethyloxycarbonyl the indole ring closure produces a 2-ethyloxycarbonylindol-3-ylalkanoic acid ester which can be hydrolyzed to the corresponding 2-carboxyindol-3-ylalkanoic acid which then can be decarboxylated to produce the unsubstituted indolylalkanoic acid.

The indol-3-yl($C_{2-4}$)alkylamines of Formula III can be then prepared by heating an appropriate indolyl(-$C_{3-5}$)alkanoic acid in the presence of methanol until the methyl indolyl($C_{3-5}$)alkanoate is formed, reacting the alkanoate with hydrazine hydrate in alcohol to form the indol-3-yl($C_{3-5}$)alkyl hydrazide, thoroughly drying the hydrazide by evaporating in dry benzene under vacuum and then heating the residue in absolute methanol until the methyl indol-3-yl($C_{2-4}$)alkyl carbamate is formed, reacting the carbamate with phthalic anhydride to form the indol-3-yl($C_{2-4}$)alkyl phthalimide, and finally reacting the phthalimide with hydrazine in dilute alcohol to form the indol-3-yl($C_{2-4}$)alkylamine.

Appropriate phenylhydrazone derivatives can be prepared by reaction of a ketone or aldehyde of the formula

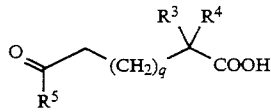

in which q, $R^3$, $R^4$ and $R^5$ are as defined in the Summary of the Invention, with optionally substituted phenylhydrazine. Phenylhydrazone derivatives in which $R^{11}$ is carboxyl can be prepared by reaction of an acetoacetic ester derivative of the formula

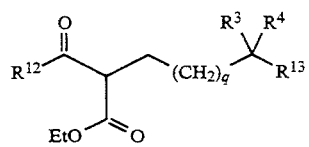

in which q, $R^3$ and $R^4$ are as defined in the Summary of the Invention and $R^{12}$ is methyl and $R^{13}$ is carboxyl or $R^{12}$ and $R^{13}$ together are a bond, with optionally substituted diazonium salt. The aldehydes, ketones, and acetoacetic esters suitable for preparing the phenylhydrazone derivatives are commercially available or can be readily prepared by one of ordinary skill in the art of organic synthesis.

Alternatively, the compounds of Formula I can be prepared by a process which comprises reacting a compound of Formula IV

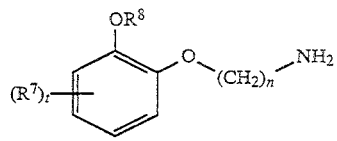

in which n, t, $R^7$ and $R^8$ are as defined above, with a compound of Formula V

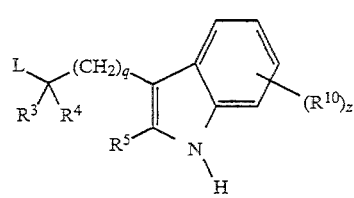

in which each L, q, $R^3$, $R^4$, $R^5$ and $R^{10}$ are as defined above, and then when necessary removing any protective groups.

Alternatively, the compounds of Formula I can be prepared by a process which comprises reacting a compound of Formula VI

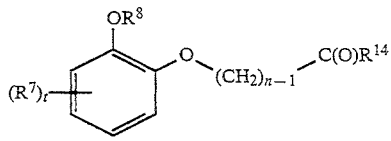

in which $R^{14}$ is hydroxy or halogen and n, t, $R^7$ and $R^8$ are as defined above, with a compound of Formula III; reducing; and when necessary removing any protective groups. The reaction is carried out in the presence of base at 0° to 62° C., to form a N-indol-3-yl($C_{2-4}$)alkyl phenoxy($C_{1-3}$)alkylamide. Suitable bases include potassium carbonate, triethylamine, pyridine, etc., preferably triethylamine. When $R^{14}$ is hydroxy the reaction is carried out in the presence of a coupling agent (e.g., dicyclohexylcarbodiimide or 2-ethyloxyl-1(2H)-quinolinecarboxylic acid). Suitable solvents for the reaction include methylene chloride, THF, etc., preferably methylene chloride. Suitable agents for the reduction of the amide include borane-methyl sulfide complex, lithium aluminum hydride, sodium borohydride (NaBH$_4$)-/cobalt(II) chloride (CoCl$_2$), NaBH$_4$/titanium(IV) chloride (TiCl$_4$), preferably NaBH$_4$/TiCl$_4$. Suitable solvents for the reduction include THF, ether, ethylene glycol dimethyl ether, and the like.

The compounds of Formula IV can be prepared by alkylation of the appropriate 2-alkyloxyphenol with an ($C_{1-4}$)alkyl ω-halo($C_{1-3}$)alkanoate in the presence of base (e.g., sodium hydroxide, potassium carbonate, triethylamine, etc.) and in a suitable solvent (e.g., THF, acetone, DMF, ethanol, etc.), followed by hydrolysis of the ester group with aqueous base (e.g., potassium hydroxide, sodium hydroxide, etc.) or acid (e.g., hydrochloric acid, etc.), then optional conversion into acid halide (e.g., by reacting with thionyl chloride or oxalyl chloride).

Additional Processes

Compounds of Formula I may be prepared as pharmaceutically acceptable acid addition salts by reacting the free base forms of a compound of Formula I with a pharmaceutically acceptable inorganic or organic acid. Alternatively, the pharmaceutically acceptable base addition salts of compounds of Formula I may be prepared by reacting the free acid forms of compounds of Formula I with pharmaceutically acceptable inorganic or organic bases. Inorganic and organic acids and bases suitable for the preparation of the pharmaceutically acceptable salts of compounds of Formula I are set forth in the definitions section of this application. Alternatively, the salt forms of the compounds of Formula I may be prepared using salts of the starting materials or intermediates.

The free acid or free base forms of the compounds of Formula I can be prepared from the corresponding base addition salt or acid addition salt form. For example, compounds of Formula I in an acid addition salt form may be converted to the corresponding free base by treating with a suitable base (e.g., ammonium hydroxide solution, sodium hydroxide, etc.). Compounds of Formula I in a base addition salt form may be converted to the corresponding free acid by treating with a suitable acid (e.g., hydrochloric acid, etc).

In summary, the processes for preparing the compounds of Formula I are:

(A) reacting a compound of Formula II:

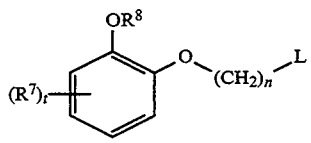

in which
n is 2, 3 or 4;
t is 0, 1, 2 or 3; each
$R^7$ is halogen, cyano, $(C_{1-8})$alkyl, $(C_{1-8})$alkyloxy or trifluoromethyl or is —$OR^9$, in which $R^9$ is a protective group; and
$R^8$ is a protective group, $(C_{1-4})$alkyl, fluoro$(C_{1-4})$alkyl, difluoro$(C_{1-4})$alkyl, trifluoro$(C_{1-4})$alkyl, $(C_{1-4})$alkyloxy$(C_{1-4})$alkyl, oxo$(C_{1-4})$alkyl, $(C_{1-8})$cycloalkyl, $(C_{1-8})$cycloalkylmethyl or allyl or phenyl$(C_{1-4})$alkyl or heterocyclo$(C_{1-8})$alkyl (optionally substituted with one to two substituents independently selected from $(C_{1-4})$alkyl, $(C_{1-4})$alkyloxy, trifluoromethyl and halogen); and
L is a leaving group; with a compound of Formula III:

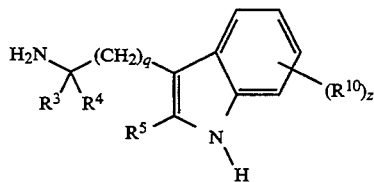

in which
q is 1, 2 or 3;
z is 0, 1, 2 or 3; and $R^3$ and $R^4$ are independently hydrogen, $(C_{1-4})$alkyl, $(C_{1-8})$cycloalkyl, $(C_{1-8})$cycloalkylmethyl or allyl; and $R^5$ is hydrogen, $(C_{1-4})$alkyl, $(C_{1-8})$cycloalkyl, $(C_{1-8})$cycloalkylmethyl, allyl, $(C_{1-4})$alkylsulfonyl and aminocarbonyl; and each $R^{10}$ is independently halogen, cyano, $(C_{1-8})$alkyl, $(C_{1-8})$alkyloxy or trifluoromethyl or is —$OR^9$, in which $R^9$ is a protective group; with the proviso that when n is 2, t is 0, q is 1, z is 0, 1 or 2, $R^5$ is hydrogen and $R^6$ is hydroxy or $(C_{1-8})$alkyloxy then at least one of $R^3$ and $R^4$ is not hydrogen; and then when necessary removing any protective groups; or (B) reacting a compound of Formula IV:

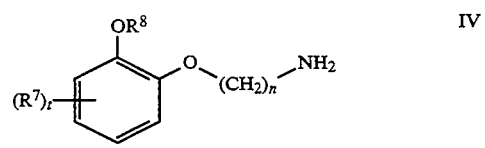

in which n, t, $R^7$, $R^8$ are as defined above, with a compound of Formula V:

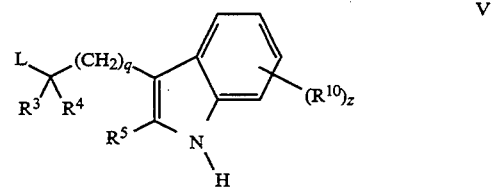

in which each L, q, $R^3$, $R^4$, $R^5$ and $R^{10}$ are as defined above, and then when necessary removing any protective groups; or (C) reacting a compound of Formula VI:

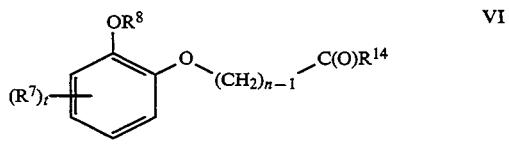

in which $R^{14}$ is hydroxy or halogen and n, t, $R^7$ and $R^8$ are as defined above, with a compound of Formula III; reducing; and when necessary removing any protective groups; or (D) converting a non-salt form of a compound of Formula I to the corresponding pharmaceutically acceptable salt form; or (E) converting a pharmaceutically acceptable salt form of a compound of Formula I to the corresponding non-salt form.

In any of the above last step processes, a reference to Formula I refers to such Formula wherein n, q, t, z, $R^1$, $R^2$, $R^3$, $R^4$, $R^5$ and $R^6$ are as defined in their broadest definitions set forth in the Summary of the Invention, with the processes applying particularly well to the presently preferred embodiments.

EXAMPLE 1

2-(Cyclopropylmethyloxy)phenoxyethyl Methanesulfonate

The following is the preparation of a compound of Formula II in which n is 2, t is 0, $R^2$ is cyclopropylmethyl, and L is methanesulfonate.

Step (a)

2-Hydroxy-1-(2-hydroxyethyloxy)benzene (4 g, 26.0 mmol), cyclopropylmethyl-bromide (5.0 g, 37.0 mmol), and potassium carbonate (5.0 g, 36.2 mmol) were combined in acetone (80 mL) and the mixture was refluxed for 18 hours. The mixture was cooled and filtered. The filtrate was evaporated and the residue was dissolved in ether. The solution was washed with water 2N sodium hydroxide, and then brine, and dried over magnesium sulfate. Evaporation gave 2-cyclopropylmethyloxy-1-(2-hydroxyethyloxy)benzene (6.2 g) as an oil.

Step (b)

2-Cyclopropylmethyloxy-1-(2-hydroxyethyloxy)benzene (2.7 g, 13.0 mmol), prepared as in Example 1, Step (a), and triethylamine (2.7 mL, 19.5 mmol) were dissolved in methylene chloride (20 mL) and the solution was cooled in an ice bath. Methanesulfonyl chloride (1.2 mL, 15.5 mmol) in methylene chloride (10 mL) was added dropwise to the solution and the mixture was stirred at 0° C. for 30 minutes. Water was added and the mixture was stirred vigorously at room temperature for 15 minutes. The mixture was extracted into methylene chloride. The organic phase was separated, washed with 2N hydrochloric acid and then brine, and dried over magnesium sulfate. Evaporation gave 2-[2-(cyclopropylmethyloxy)phenoxy]ethyl methanesulfonate (3.7 g, 12.9 mmol) as a white solid, m.p. 90°–91° C.

Proceeding as in Example 1, Step (b) but replacing 2-cyclopropylmethyloxy-1-(2-hydroxyethyloxy)benzene with 2-diphenylmethyloxy-1-(2-hydroxyethyloxy)benzene gave 2-(2-diphenylmethyloxyphenoxy)ethyl methanesulfonate.

Proceeding as in Example 1, Step (a), but replacing cyclopropylmethylbromide with iodomethane, and then correspondingly as in Example 1, Step (b), gave 2-(2-methyloxyphenoxy)ethyl methanesulfonate, m.p. 75°–76° C.

Proceeding as in Example 1, Step (a), but replacing cyclopropylmethylbromide with iodoethane, and then correspondingly as in Example 1, Step (b), gave 2-(2-ethyloxyphenoxy)ethyl methanesulfonate.

Proceeding as in Example 1, Step (a), but replacing cyclopropylmethylbromide with 2-iodo-1,1,1-trifluoroethane, and then correspondingly as in Example 1, Step (b), gave 2-[2-(2,2,2-trifluoroethyloxy)phenoxy]ethyl methanesulfonate, m.p. 36°–38° C.

Proceeding as in Example 1, Step (a), but replacing cyclopropylmethylbromide with 2-bromopropane, and then correspondingly as in Example 1, Step (b), gave 2-[2-(prop-2-yloxy)phenoxy]ethyl methanesulfonate.

Proceeding as in Example 1, Step (a), but replacing cyclopropylmethylbromide with iodobutane, and then correspondingly as in Example 1, Step (b), gave 2-[2-(but-1-yloxy)phenoxy]ethyl methanesulfonate.

Proceeding as in Example 1, Step (a), but replacing cyclopropylmethylbromide with 1-iodo-2-methylpropane, and then correspondingly as in Example 1, Step (b), gave 2-[2-(2-methylprop-1-yloxy)phenoxy]ethyl methanesulfonate, m.p. 59°–61° C.

Proceeding as in Example 1, Step (a), but replacing cyclopropylmethylbromide with 3-bromopropene, and then correspondingly as in Example 1, Step (b), gave 2-[2-(2-propenyloxy)phenoxy]ethyl methanesulfonate, m.p. 61°–63° C.

Proceeding as in Example 1, Step (a) but replacing cyclopropylmethylbromide with 1-bromo-2-methyloxyethane, and then correspondingly as in Example 1, Step (b), gave 2-[2-(2-methyloxyethyloxy)phenoxy]ethyl methanesulfonate.

Proceeding as in Example 1, Step (a), but replacing cyclopropylmethylbromide with bromomethylbenzene, and then correspondingly as in Example 1, Step (b), gave 2-(2-benzyloxyphenoxy)ethyl methanesulfonate, m.p. 98°–100° C.

Proceeding as in Example 1, Step (a), but replacing cyclopropylmethylbromide with bromomethylbenzene and 2-hydroxy-1-(2-hydroxyethyloxy))benzene with 2-hydroxy-1-(3-hydroxyprop-1-yloxy)benzene, and then correspondingly as in Example 1, Step (b), gave 3-(2-benzyloxyphenoxy)prop-1-yl methanesulfonate.

Proceeding as in Example 1, Step (a), but replacing cyclopropylmethylbromide with 2-(2-bromomethyl)tetrahydrofuran, and then correspondingly as in Example 1, Step (b), gave 2-[2-(tetrahydrofur-2-ylmethyloxy)phenoxy]ethyl methanesulfonate.

Proceeding as in Example 1, Step (a), but replacing cyclopropylmethylbromide with 2-bromoacetone, and then correspondingly as in Example 1, Step (b), gave 2-[2-(2-oxoprop-1-yloxy)phenoxy]ethyl methanesulfonate.

Proceeding as in Example 1, Step (a), but replacing cyclopropylmethylbromide with 1-iodo-2-methylpropane and 2-hydroxy-1-(2-hydroxyethyloxy)benzene with 4-fluoro-2-hydroxy-1-(2-hydroxyethyloxy)benzene, and then correspondingly as in Example 1, Step (b), gave 2-[4-fluoro-2-(2-methylprop-1-yloxy)phenoxy]ethyl methanesulfonate.

Proceeding as in Example 1, Step (a), but replacing cyclopropylmethylbromide with 1-iodo-2-methylpropane and 2-hydroxy-1-(2-hydroxyethyloxy)benzene with 5-fluoro-2-hydroxy-1-(2-hydroxyethyloxy)benzene, and then correspondingly as in Example 1, Step (b), gave 2-[5-fluoro-2-(2-methylprop-1-yloxy)phenoxy]ethyl methanesulfonate, m.p. 53°–55° C.

Proceeding as in Example 1, Step (a), but replacing cyclopropylmethylbromide with 1-iodo-2-methylpropane and 2-hydroxy-1-(2-hydroxyethyloxy)benzene with 2-hydroxy-1-(2-hydroxyethyloxy)-5-diphenylmethyloxybenzene, and then correspondingly as in Example 1, Step (b), gave 2-[2-(2-methylprop-1-yloxy)-5-diphenylmethyloxyphenoxy]ethyl methanesulfonate.

EXAMPLE 2

[2-(5-Chloro-1H-indol-3-yl)-1,1-dimethylethyl]amine

The following is the preparation of a compound of Formula III in which z is 1, q is 1, $R^3$ and $R^4$ are each methyl, $R^5$ is hydrogen and $R^6$ is chloro at the 5-position.

Step (a)

Aqueous dimethylamine (8.0 mL, 63.7 mmol) and aqueous formaldehyde (4.8 mL, 64.0 mL) were combined in dioxane (50 mL) and acetic acid (50 mL). 5-Chloro-1H-indole (9.5 g, 62.5 mmol) in dioxane (30 mL) was added dropwise to the mixture, which was then was stirred at room temperature for 18 hours. The mixture was concentrated to approximately 50 mL by rotary evaporation, diluted with water ($\approx$500 mL), and extracted with ether ($\sim$200 mL). The aqueous phase was separated, cooled, made basic with sodium hydroxide, and extracted into methylene chloride. The methylene chloride phase was separated, washed with water and then brine, dried over potassium carbonate, filtered, and evaporated. Crystallization from a mixture of acetone and diisopropyl ether gave 3-(dimethylaminomethyl)-5-chloro-1H-indole (10.6 g, 50.5 mmol) as white crystals, m.p. 148°–150° C.

Step (b)

5-Chloro-3-(dimethylaminomethyl)-1H-indole (10.6 g, 50.5 mmol), prepared as in Example 2, Step (a) and powdered sodium hydroxide (3.0 g, 75.0 mmol) were combined in 2-nitropropane (80 mL, 890.8 mmol) and the mixture was stirred at 120° C. and under nitrogen for 20 hours. The mixture was cooled, acidified with 10% acetic acid (80 mL), stirred at room temperature for 1 hour, and then extracted into ether. The organic phase was separated, washed with water and then brine, dried over magnesium sulfate, and evaporated. Filtration of the residue through a short column of silica gel gave 3-(2,2-dimethyl-2-nitroethyl)-5-chloro-1H-indole (13.5 g, 53.1 mmol) as a yellow oil.

Step (c)

5-Chloro-3-(2,2-dimethyl-2-nitroethyl)-1H-indole (13.5 g, 53.1 mmol), prepared as in Example 2, Step (b), was dissolved in ethanol ($\approx$100 mL). An aqueous suspension of RANEY NICKEL® catalyst (5.0 mL) was added to the solution and the mixture was heated to 80° C. Hydrazine hydrate (10 mL, 321.1 mmol) in ethanol ($\approx$30 mL) was added dropwise to the mixture which was then stirred for an additional 30 minutes. The mixture was filtered through celite and the filter cake was washed with methanol. The filtrate was concentrated by rotary evaporation to $\approx$75 mL. Crystallization upon addition of water gave [2-(5-chloro-1H-indol-3-yl)-1,1-dimethylethyl]amine (9.17 g, 40.9 mmol), m.p. 156°–158° C.

Proceeding as in Example 2, Step (a), but replacing 5-chloro-1H-indole with 1H-indole, and then correspondingly as in Example 2, Steps (b) and (c), gave [2-(1H-indol-3-yl)-1,1-dimethylethyl]amine, m.p. 75°–76° C.

Proceeding as in Example 2, Step (a), but replacing 5-chloro-1H-indole with 6-fluoro-1H-indole, and then correspondingly as in Example 2, Steps (b) and (c), gave [2-(6-fluoro-1H-indol-3-yl)-1,1-dimethylethyl]amine, m.p. 115°–117° C.

Proceeding as in Example 2, Step (a), but replacing 5-chloro-1H-indole with 6-diphenylmethyloxy-1H-indole, and then correspondingly as in Example 2, Steps (b) and (c), gave [2-(6-diphenylmethyloxy-1H-indol-3-yl)-1,1-dimethylethyl]-amine.

Proceeding as in Example 2, Step (a), but replacing 5-chloro-1H-indole with 5,6-dimethyloxy-1H-indole, and then correspondingly as in Example 2, Steps (b) and (c), gave [2-(5,6-dimethyloxy-1H-indol-3-yl)-1,1-dimethylethyl]amine.

Proceeding as in Example 2, Step (a), but replacing 5-chloro-1H-indole with 2-aminocarbonyl-1H-indole, and then correspondingly as in Example 2, Steps (b) and (c), gave [2-(2-aminocarbonyl-1H-indol-3-yl)-1,1-dimethylethyl]amine.

Proceeding as in Example 2, Step (a), but replacing 5-chloro-1H-indole with 2-methylsulfonyl-1H-indole, and then correspondingly as in Example 2, Steps (b) and (c), gave [2-(2-methylsulfonyl-1H-indol-3-yl)-1,1-dimethylethyl]-amine, m.p. 129.5°–130.5° C.

Proceeding as in Example 2, Step (a), but replacing 5-chloro-1H-indole with 2-methyl-1H-indole, and then correspondingly as in Example 2, Steps (b) and (c), gave [2-(2-methyl-1H-indol-3-yl)-1,1-dimethylethyl]amine, m.p. 97°–98° C.

Proceeding as in Example 2, Step (a), but replacing 5-chloro-1H-indole with 2,5-dimethyl-1H-indole, and then correspondingly as in Example 2, Steps (b) and (c), gave [2-(2,5-dimethyl-1H-indol-3-yl)-1,1-dimethylethyl]amine, m.p. 124°–126° C.

Proceeding as in Example 2, Step (a), but replacing 5-chloro-1H-indole with 5-methyloxy-2-methyl-1H-indole, and then correspondingly as in Example 2, Steps (b) and (c), gave [1-(5-methyloxy-2-methyl-1H-indol-3-yl)-1,1-dimethylethyl]amine, m.p. 130°–132° C.

Proceeding as in Example 2, Step (a), but replacing 5-chloro-1H-indole with 5-chloro-2-methyl-1H-indole, and then correspondingly as in Example 2, Steps (b)and (c), gave [1-(5-chloro-2-methyl-1H -indol-3-yl)-1,1-dimethylethyl]amine, m.p. 128°–130° C.

EXAMPLE 3

[2-(5-chloro-1H-indol-3-yl)-1,1-dimethylethyl]-[2-(2-Cyclopropylmethyloxyphenoxy)ethyl]amine The following is the preparation of a compound of Formula I in which n is 2, q is 1, t is 0, z is 1, $R^2$ is cyclopropylmethyl, $R^3$ and $R^4$ are each methyl, $R^5$ is hydrogen, and $R^6$ is chloro at the 5-position.

2-[2-(cyclopropylmethyloxy)phenoxy]ethyl methanesulfonate (8.0 g, 28.0 mmol) and potassium iodide (4.65 g, 28.0 mmol) were combined in DMF and the mixture was stirred at 120° C. for 15 minutes. [2-(5-Chloro-1H-indol-3-yl)-1,1-dimethyl-ethyl]amine (4.77 g, 21.7 mmol) and potassium carbonate (5.8 g, 42.0 mmol) were added to the mixture, which was then diluted with DMF ($\approx$50 mL) and stirred at 130°–135° C. and under nitrogen for 2 hours. The mixture was cooled, poured into water ($\approx$800 mL), and then extracted into ether. The organic phase was separated, washed once with water and then brine, dried over magnesium sulfate, and evaporated. The residue was dissolved in ethyl acetate, 5% hydrochloric acid in methanol was added, and the solution was evaporated. The residue was dissolved in ethyl acetate and a small amount of methanol and the solution was evaporated. The residue was again dissolved in ethyl acetate and methanol and the solution was evaporated. Filtration gave [2-(5-chloro-1H-indol-3-yl)-1,1-dimethylethyl][2-(2-cyclopropylmethyloxyphenoxy)ethyl]amine hydrochloride (7.8 g, 17.4 mmol), m.p. 199°–201° C.

Proceeding as in Example 3, but replacing 2-[2-(cyclopropylmethyloxy)phenoxy]ethyl methanesulfonate with 2-[2-(2,2,2-trifluoroethyloxy)phenoxy]ethyl methanesulfonate, gave [2-(5-chloro-1H-indol-3-yl)-1,1-dimethylethyl]-{2-[2-(2,2,2-trifluoroethyloxy)phenoxy]ethyl}amine hydrochloride, m.p. 152°–154° C.

Proceeding as in Example 3, but replacing [2-(5-chloro-1H-indol-3-yl)-1,1-dimethyethyl]amine with [2-(1H-indol-3-yl) -1,1-dimethylethyl]amine, gave [2-(1H-indol-3-yl)-1,1-dimethylethyl][2-(2-cyclopropylmethyloxyphenoxy)ethyl]amine hydrochloride, m.p. 166°–168° C.

Proceeding as in Example 3, but replacing [2-(5-chloro-1H-indol-3-yl)-1,1-dimethyethyl]amine with [2-(2-methyl-1H-indol-3-yl)-1,1-dimethylethyl]amine, gave [2-(2-methyl-1H-indol-3-yl)-1,1-dimethylethyl][2-

(2-cyclopropylmethyloxyphenoxy)ethyl]amine hydrochloride, m.p. 160°–162° C.

Proceeding as in Example 3, but replacing [2-(5-chloro-1H-indol-3-yl)-1,1-dimethyethyl]amine with [2-(6-fluoro-1H-indol-3-yl)-1,1-dimethylethyl]amine, gave [2-(2-fluoro-1H-indol-3-yl)-1,1-dimethylethyl][2-(2-cyclopropylmethyloxyphenoxy)ethyl]amine hydrochloride, m.p. 184°–186° C.

Proceeding as in Example 3, but replacing [2-(5-chloro-1H-indol-3-yl)-1,1-dimethyethyl]amine with [2-(6-fluoro-1H-indol -3-yl)-1-methylethyl]amine, gave [2-(2-fluoro-1H-indol-3-yl)-1-methylethyl][2-(2-cyclopropylmethyloxyphenoxy)-ethyl]amine hydrochloride.

Proceeding as in Example 3, but replacing 2-[2-(cyclopropylmethyloxy)phenoxy]ethyl methanesulfonate with 2-(2-methyloxyphenoxy)ethyl methanesulfonate and [1-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl][2- (2-methyloxyphenoxy)ethyl]amine hydrochloride, m.p. 156°–158° C.

Proceeding as in Example 3, but replacing 2-[2-(cyclopropylmethyloxy)phenoxy]ethyl methanesulfonate with 2-(2-ethyloxyphenoxy)ethyl methanesulfonate and [2-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl][2-(2-ethyloxyphenoxy)ethyl]amine hydrochloride, m.p. 184°–186° C.

Proceeding as in Example 3, but replacing 2-[2-(cyclopropylmethyloxy)phenoxy]ethyl methanesulfonate and [2-(5-chloro-1H-indol-3-yl)-1,1-dimethylethyl]amine with [2-(1H-indol-3-yl)-ethyl]amine, gave [2-(1H-indol-3-yl)ethyl][2-(2-ethyloxyphenoxy)ethyl]amine hydrochloride, m.p. 134°–135° C.

Proceeding as in Example 3, but replacing 2-[2-(cyclopropylmethyloxy)phenoxy]ethyl methanesulfonate with 2-(2-ethyloxyphenoxy)ethyl methanesulfonate and [2-(5-chloro-1H-indol-3-yl)-1,1-dimethylethyl]amine with [3-(1H-indol-3-yl)-prop-1-yl]amine, gave [3-(1H-indol-3-yl)prop-1-yl][2-(2-ethyloxyphenoxy)ethyl]amine hydrochloride, m.p. 147°–148° C.

Proceeding as in Example 3, but replacing 2-(cyclopropylmethyloxy)phenoxyethyl methanesulfonate with 2-[2-(prop-2-yloxy)phenoxy]ethyl methanesulfonate and [2- (5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl]{2- [2-(prop-2-yloxy)phenoxy]ethyl}amine hydrochloride, m.p. 164°–166° C.

Proceeding as in Example 3, but replacing 2-[2-(cyclopropylmethyloxy)phenoxy]ethyl methanesulfonate with 2-[2-(but-1-yloxy)phenoxy]ethyl methanesulfonate and [2-(5-chloro-1H-indol-3-yl)-1,1-dimethylethyl]amine with [2-(1H-indol-3-yl)-2-methylprop-1-yl]amine, gave [2-(1H-indol-3-yl)-1,1-dimethylethyl]{2-[2-(but-1-yloxy)phenoxy]ethyl}amine hydrochloride, m.p. 150°–152° C.

Proceeding as an Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2- (1H-indol-3-yl)-1,1-dimethylethyl]amine, gave [2-(1H-indol-3-yl)-1,1-dimethylethyl]{-[2-(2-methylprop-1-yloxy)phenoxy]ethyl}amine hydrochloride, m.p. 147°–148° C.

Proceeding as an Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2-(2-aminocarbonyl-1H-indol-3-yl)-1,1-dimethylethyl]amine, gave [2-(2-aminocarbonyl-1H-indol-3-yl)-1,1-dimethylethyl]{2-[2-(2-methylprop-1-yloxy)phenoxy]ethyl}amine hydrochloride, m.p. 154°–156° C.

Proceeding as an Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2-(2-methylsulfonyl-1H-indol-3-yl)-1,1-dimethylethyl]amine, gave [2-(2-methylsulfonyl -1H-indol-3-yl)-1,1-dimethylethyl]{2-[2-(2-methylprop-1-yloxy)phenoxy]ethyl}amine hydrochloride.

Proceeding as an Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2- (6-fluoro-1H-indol-3-yl)-1,1-dimethylethyl]amine, gave [2-(6-fluoro-1H-indol-3-yl)-1,1-dimethylethyl]{2-[2-(2-methyl-prop-1-yloxy)-phenoxy]ethyl}amine hydrochloride, m.p. 135°–137° C.

Proceeding as in Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2-(5,6-dimethyloxy-1H-indol-3-yl)-1,1-dimethylethyl]amine, gave [2-(5,6-dimethyloxy-1H-indol-3-yl)-1,1-dimethylethyl]{2-[2-(2-prop-1-yloxy)phenoxy]ethyl}amine hydrochloride.

Proceeding as in Example 3, but replacing 2-[2-(cyclopropylmethyloxy)phenoxy]ethyl methanesulfonate with 2-[2-(2-methylprop-1-yloxy)phenoxy]ethyl methanesulfonate and [2 -(5-chloro-1H-indol-3-yl)-1,1-dimethylethyl]amine with [2-(2,5-dimethyl-1H-indol-3-yl)-1,1-dimethylethyl]amine, gave [2-(2,5-dimethyl-1H-indol-3-yl)-1,1-dimethylethyl]{2-[2-(2-methylprop-1-yloxy)phenoxy]ethyl}amine hydrochloride, m.p. 216°–218° C.

Proceeding as in Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2-(5-methyloxy-2-methyl-1H-indol-3-yl)-1,1-dimethylethyl]amine, gave [2-(5-methyloxy-2-methyl-1H-indol-3-yl)-1,1-dimethylethyl]{2-[2-methylprop-1-yloxy)phenoxy]ethyl}amine hydrochloride, m.p. 184°–186° C.

Proceeding as in Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2-(5-chloro-2-methyl-1H-indol-3-yl)-1,1-dimethylethyl]amine, gave [2-(5-chloro-2-methyl-1H-indol-3-yl)-1,1-dimethylethyl]{2-[2-(2-methyl-prop-1-yloxy)phenoxy]ethyl}amine hydrochloride, m.p. 202°–204° C.

Proceeding as in Example 3, but replacing 2-[2-(cyclopropylmethyloxy)phenoxy]ethyl methanesulfonate with 2-[4-fluoro-2-(2-methylprop-1-yloxy)phenoxy]ethyl methanesulfonate and [2-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl]{2-[4-fluoro-2-(2-methylprop-1-yloxy)-phenoxy]ethyl}amine hydrochloride, m.p. 155°–156° C.

Proceeding as in Example 3, but replacing 2-[2-(cyclopropylmethyloxy)phenoxy]ethyl methanesulfonate with 2-[5-fluoro-2-(2-methylprop-1-yloxy)phenoxy]ethyl methanesulfonate and [2-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl]{2-[5-fluoro-2-(2-methylprop-1-yloxy)-phenoxy ethyl}amine hydrochloride, m.p. 171°–174° C.

Proceeding as in Example 3, but replacing 2-[2-(cyclopropylmethyloxy)phenoxy]ethyl methanesulfonate with 2-[2-(2-propenyloxy)phenoxy]ethyl methanesulfonate and [2-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl]{2-[2-(2-propenyloxy)phenoxy]ethyl}amine hydrochloride, m.p. 55°–156° C.

Proceeding as in Example 3, but replacing 2-[2-(cyclopropylmethyloxy)phenoxy]ethyl methanesulfonate with 2-[2-(2-methoxethyloxy)phenoxy]ethyl methanesulfonate and [2-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl]{2-[2-(2-methyloxyethyloxy)phenoxy]ethyl}amine hydrochloride, m.p. 166°–168° C.

Proceeding as in Example 3, but replacing 2-[2-(cyclopropylmethyloxy)phenoxy]ethyl methanesulfonate and [2-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl]{2-[2-(2- oxopropyloxy)phenoxy]ethyl}amine hydrochloride.

Proceeding as in Example 3, but replacing 2-[2-(cyclopropylmethyloxy)phenoxy]ethyl methanesulfonate with 2-(2-benzyloxyphenoxy)ethyl methanesulfonate and [2- (5-chloro-1H-indol-3-yl)-1,1-dimethylethyl]amine with [2-(1H-indol-3yl)-1,1-dimethylethyl]amine, gave [2-(1H-indol-3-yl)-1,1-dimethylethyl]{2- (2-benzyloxyphenoxy)ethyl}amine hydrochloride, m.p. 148°–150° C.

Proceeding as in Example 3, but replacing 2-[2-(cyclopropylmethyloxy)phenoxy]ethyl methanesulfonate with 3-(2-benzyloxyphenoxy)prop-1-yl methanesulfonate and [2-(5-chloro-1H-indol-3-yl)-1,1-dimethylethyl]amine with [2- (1H-indol-3-yl)-1,1-dimethylethyl]amine, gave [2-(1H-indol-3-yl)-1,1-dimethylethyl]{3-(2-benzyloxyphenoxy)prop-1-yl}amine hydrochloride.

Proceeding as in Example 3, but replacing 2-[2-(cyclopropylmethyloxy)phenoxy]ethyl methanesulfonate with 2-[2-(tetrahydrofur-2-ylmethyloxy)phenoxy]ethyl methanesulfonate and [2-(5-chloro-1H-indol-3-yl)-1,1-dimethylethyl]amine with [2-(1H-indol-3-yl)-1,1-dimethylethyl]amine, gave [2-(1H-indol-3-yl)-1,1-dimethylethyl]{2-[2-(tetrahydrofur-2-ylmethyloxy)phenoxy]ethyl}amine hydrochloride.

Proceeding as in Example 3, but replacing 2-[2-(cyclopropylmethyloxy)phenoxy]ethyl methanesulfonate with 2-[2-(diphenylmethyloxy)phenoxy]ethyl methanesulfonate and [2-(5-chloro-1H-indol-3-yl)-1,1-dimethylethyl]amine with [2-(1H-indol-3-yl)-1,1-dimethylethyl]amine, and then deprotecting, gave [2-(1H-indol-3-yl)-1,1-dimethylethyl][2- (2-hydroxyphenoxy)ethyl]amine hydrochloride.

Proceeding as in Example 3, but replacing 2-[2-(cyclopropylmethyloxy)phenoxy]ethyl methanesulfonate with 2-[2-(2-methylprop-1-yloxy)phenoxy]ethyl methanesulfonate and [2-(5-chloro-1H-indol-3-yl)-1,1-dimethylethyl]amine with [2-(6-diphenylmethyloxy-1H-indol-3-yl)-1,1-dimethylethyl]amine and then removing the protective group, gave [2-(6-hydroxy-1H-indol-3-yl)-1,1-dimethylethyl]{2-[2-(2-methylprop-1-yloxy)-phenoxy]ethyl}amine hydrochloride.

Proceeding as in Example 3, but replacing 2-[2-(cyclopropylmethyloxy)phenoxy]ethyl methanesulfonate with 2- [5-diphenylmethyloxy-2-(2-methylprop-1-yloxy)phenoxy]ethyl methanesulfonate and [2-(5-chloro-1H-indol-3-yl)-1,1-dimethylethyl]amine with [2-(1H-indol-3-yl)-1,1-dimethylethyl]amine and then removing the protective group, gave [2-(1H-indol-3-yl)-1,1-dimethylethyl]{2-[5-hydroxy-2-(2-methylprop-1-yloxy)-phenoxy]ethyl}amine hydrochloride.

EXAMPLE 5

The following are representative pharmaceutical formulations containing a compound of Formula I.

ORAL FORMULATION

A representative solution for oral administration contains:

| | |
|---|---|
| Compound of Formula I | 100–1000 mg |
| Citric Acid Monohydrate | 105 mg |
| Sodium Hydroxide | 18 mg |
| Flavoring | |
| Water | q.s. to 100 mL |

INTRAVENOUS FORMULATION

A representative solution for intravenous administration contains:

| | |
|---|---|
| Compound of Formula I | 10–100 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

TABLET FORMULATION

A representative tablet form of a compound of Formula I may contain:

| | |
|---|---|
| Compound of Formula I | 1% |
| Microcrystalline Cellulose | 73% |
| Stearic Acid | 25% |
| Colloidal Silica | 1% |

EXAMPLE 6

$\alpha_1$-Adrenergic Receptor Binding Assays

The following describes in vitro assays in rat submaxillary gland and liver membrane preparations to identify test compounds with affinity for $\alpha_1$-adrenergic receptors.

Step (a): Membrane Preparation

Rat submaxillary gland or liver tissue (obtained from Pel Freez) were placed in 5 to 6 volumes (w/v) of homogenizing buffer (50 mM Tris hydrochloride and 5 mM EDTA disodium salt; all buffers used in the membrane preparation were pH 7.4 and 4° C.). The tissue was homogenized with a Waring blender (30 seconds at high setting) and then with a Polytron P10 tissue disrupter (twice, 10 seconds at setting 10). The homogenate was filtered twice through cheesecloth and centrifuged with a RC5C centrifuge (10 minutes at 2100 rpm). The supernatant was removed by aspiration and stored on ice.

The pellet was placed in 2 to 3 volumes of homogenizing buffer and homogenized with a Polytron P10 tissue disrupter (twice, 10 seconds at setting 5). The homogenate was centrifuged with a RCSC centrifuge (10 minutes at 2100 rpm) and the supernatant was removed by aspiration. The combined supernatants were centrifuged with a RCSC centrifuge using a SS34 rotor (15 minutes at 19,500 rpm) and the supernatant was removed by decanting.

The pellet was placed in an amount of homogenizing buffer equivalent to that used to originally suspend the tissue (original volume) and homogenized with a Polytron P10 tissue disrupter (5 seconds at setting 5). The homogenate was centrifuged with a RCSC centrifuge using a SS34 rotor (15 minutes at 19,500 rpm) and the supernatant was removed by decanting.

The pellet was placed in an original amount of resuspension buffer (50 mM Tris hydrochloride and 0.5 mM EDTA free acid) and homogenized with a Polytron P10 tissue disrupter (5 seconds at setting 5). The homogenate was centrifuged with a RC5C centrifuge using a SS34 rotor (15 minutes at 19,500 rpm) and the supernatant was removed by decanting.

The procedure described in the preceding paragraph was repeated and the resulting pellet was placed in a small amount of resuspension buffer and homogenized for 5 seconds with a Polytron P10 tissue disrupter at setting 5. The excess of homogenated was rinsed from the polytron with a small volume of resuspension buffer such that the final volume of buffer equals 1 mL per 10 submaxillary glands or 1 mL per 0.5 G of liver tissue. The homogenate was then separated into 1 mL aliquots and stored under liquid nitrogen until required.

Step (b): Competition Assay

Aliquots of membrane homogenates, prepared as in Example 6, Step (a), were warmed to 25° C. and resuspended. Membrane homogenates were then diluted into assay buffer (50 mM Tris hydrochloride and 0.5 mM EDTA free acid; pH 7.4 and 25° C.) to a previously determined optimal dilution such that when the assay is performed less than 20% of total [$^3$H]prazosin present is bound, specific binding (i.e., total binding of [$^3$H]prazosin less binding of [$^3$H]prazosin not displaceable by $1 \times 10^{-5}$M phentolamine) is at least 10 times background (i.e., 23 dpm), and the best ratio of specific binding to total binding is obtained.

Membrane homogenate (optimal dilution, 0.15 mL), assay buffer (0.6 mL), [$^3$H]prazosin (0.3 nM in assay buffer, 0.2 mL), and phentolamine (0.2 mM in assay buffer, 0.05 mL) were combined in assay tubes (1.0 mL polystyrene microliter plates or 1.0 mL tubestrips) to measure nonspecific binding of 0.06 nM [$^3$H]prazosin (i.e., binding of [$^3$H]prazosin not displaceable by $1 \times 10^{-5}$M phentolamine). Membrane homogenate (optimal dilution; 0.15 mL), assay buffer (0.65 mL) and [$^3$H]prazosin (0.3 nM in assay buffer, 0.2 mL) were combined in assay tubes to measure total binding of 0.06 nM [$^3$H]prazosin in the absence of test compound. Membrane homogenate (optimal dilution, 0.05 mL), assay buffer (0.6 mL), [$^3$H]prazosin (0.3 nM, 0.2 mL), and test compound (2.0 nM to 2.0 mM in assay buffer, 0.05 mL) were combined in assay tubes to measure total binding of 0.06 nM [$^3$H]prazosin in the presence of each concentration of test compound.

The assay mixtures were incubated at 25° C. for 60 minutes and then filtered over 0.1% poly(ethylenimine) pretreated glass fibre filtermats using a Brandel cell harvester. Each filter was then placed in a scintillation vial with 4 mL of Aquasol scintillation cocktail and the radioactive count of each filter was determined with a scintillation counter.

Step (c): Data Reduction

The concentration of test compound necessary to displace 50% of [$^3$H]prazosin specific binding (IC$_{50}$) was determined by iterative curve fitting techniques. Relying on the IC$_{50}$, the assay concentration of [$^3$H]prazosin (i.e., $6 \times 10^{-5}$M), a previously determined dissociation constant for [$^3$H]prazosin (K$_d$; typically $3.9 \times 10^{-11}$M in submaxillary gland membrane preparations and $3.1 \times 10^{-11}$M in liver membrane preparations), and the relationship:

$$K_i = \frac{IC_{50}}{1 + (6 \times 10^{-11}/K_d)}$$

the affinity binding constant of the test compound was determined.

Proceeding as in Example 6, the compounds of this invention were tested found to be $\alpha_1$-adrenergic receptor ligands.

EXAMPLE 7

Rat, Isolated Aorta $\alpha_1$-Adrenergic Receptor Functional Assay

The following describes an in vitro assay which utilizes rat, isolated aortic smooth muscle to identify test compounds which are $\alpha_1$-adrenergic receptor antagonists.

Thoracic aorta were isolated from male, Sprague-Dawley rats (200–450 g) and immediately bathed in Krebs' solution (comprising in mM concentrations: NaCl, 118.5; NaHCO$_3$, 25; dextrose, 5; KCl, 4.8; CaCl$_2$, 2.5; MgSO$_4$, 1.2; KH$_2$PO$_4$, 1.2; cocaine, 0.03; and corticosterone, 0.03). Each aorta was dissected free from extraneous tissue and then a cross sectional ring approximately 3 mm in length was cut from the most proximal segment of the aorta. The aortic ring was suspended vertically in a 10 mL tissue bath and bathed in Kreb's solution which was maintained at 37° C. and constantly aerated with a 95% O$_2$ and 5% CO$_2$ gas mixture.

A resting tension of 1 g was applied to each aortic ring and thereafter periodically readjusted to maintain a 1 g resting tension throughout the course of the procedure. The aortic ring preparation was allowed to equilibrate for 60 minutes during which period the bath solution was replaced every 15 minutes. The tissue was then exposed to bath solution containing norepinephrine (0.1 $\mu$M) and once a steady state contraction was produced the tissue was exposed to bath solution free of norepinephrine, replacing the solution twice every 5 minutes for 30 minutes. The tissue was then exposed to norepinephrine in a cumulative concentration fashion. That is, the tissue was exposed to bath solution containing a threshold concentration of norepinephrine until a steady state contractile response was attained and then the concentration of norepinephrine was cumulatively increased by 0.5 log increments until a maximal or near maximal response was attained. Norepinephrine produces a concentration-dependent, $\alpha_1$-adrenergic receptor mediated contraction of aorta.

The tissue was then exposed to solution free of norepinephrine, replacing the solution twice every 5 minutes for 30 minutes. After baseline tension was established and readjusted to 1 g, the tissue was exposed to bath solution containing the test compound, replacing the solution every 15 minutes for 60 minutes. Then, in the presence of the test compound, the tissue was exposed to norepinephrine in a cumulative concentration fashion, increasing the norepinephrine concentration until a maximal or near maximal response was achieved.

The concentration ratio (CR) of norepinephrine necessary to produce equiactive responses in the absence and presence of the test compound was determined. Relying on the concentration ratio, the assay concentration (molar) of the test compound, and the relationship:

$$K_B = \frac{[\text{test compound}]}{CR - 1}$$

the dissociation constant ($K_B$) for the test compound was estimated.

Proceeding as in Example 7, compounds of this invention were tested and found to be $\alpha_1$-adrenergic receptor antagonists.

EXAMPLE 8

Rat, Isolated Perfused Kidney $\alpha_1$-Adrenergic Receptor Functional Assay

The following describes an in vitro assay which utilizes rat, isolated perfused kidney to identify test compounds which are $\alpha_1$-adrenergic receptor antagonists.

Sprague-Dawley rats (200–300 g) were anesthetized with sodium pentobarbital (60 mg/kg, i.p.) and the right kidney and renal artery were isolated. Each kidney was perfused via the renal artery at a constant rate of 6 mL/minute with Krebs' solution (comprising in mM concentrations: NaCl, 118.5; $NaHCO_3$, 25; dextrose, 5; KCl, 4.8; $CaCl_2$, 2.5; $MgSO_4$, 1.2; and $KH_2PO_4$, 1.2) maintained at 37° C. and constantly aerated with a 95% $O_2$ and 5% $CO_2$ gas mixture.

The preparation was allowed to equilibrate for 30 minutes and then the kidney was exposed to norepinephrine in a noncumulative concentration fashion. That is, the kidney was perfused with Krebs' solution containing norepinephrine until a steady state vasoconstrictor response was attained and then with Krebs' solution free of norepinephrine until baseline perfusion pressure was re-established. This drug cycle was repeated, incrementally increasing the concentration of norepinephrine in the perfusate by 0.5 log intervals, until a maximal or near maximal vasoconstrictor response was attained.

The kidney was perfused with Krebs' solution free of norepinephrine until baseline perfusion pressure was established and then with Krebs' solution containing test compound for 60 minutes. In the presence of the test compound, the kidney was exposed to norepinephrine in a noncumulative fashion until a maximal or near maximal pressor response was attained.

The concentration ratio of norepinephrine necessary to produce equiactive vasoconstrictor responses in the absence and presence of the test compound was determined. Relying on the concentration ratio and the assay concentration of the test compound the dissociation constant ($K_B$) for the test compound was estimated.

Proceeding as in Example 8, compounds of this invention were tested and found to be $\alpha_1$-adrenergic receptor antagonists.

EXAMPLE 9

Rabbit, Intraocular Pressure Assay

The following describes an in vivo assay which is used to identify the intraocular hypotensive effects of test compounds.

Female, New Zealand White rabbits (2–4 Kg) were randomized into assay groups of seven and proparacaine hydrochloride (0.5%) was topically administered to the cornea of both eyes. A pneumatonometer was used to measure the intraocular pressure. To acclimate the rabbits to the procedure, several sham measurements (i.e., unrecorded) were made prior to commencing the assay protocol. Control pressure measurements were then obtained and those rabbits exhibiting variations of greater than 3 mmHg were excluded from the assay.

Within one assay group, a test compound was administered in a 50 μL aliquot to one eye of each rabbit and an equal volume of vehicle was administered to the other eye (internal control). In a separate assay group, vehicle was administered in 50 μL aliquots to both eyes of the rabbits. Pressure measurements were obtained at 30 minutes post-administration and thereafter at 15 to 60 minute intervals. Evidence of ocular irritation (i.e., closure of the eyelid and/or hyperemia) were monitored.

Responses to test compounds were represented as the change from internal control. Means and standard deviations for the changes were determined for each assay group and a comparison was made between assay groups which received test compound and that which received vehicle. Significance was determined by general models.

Proceeding as in Example 9, compounds of this invention were tested and found to be hypotensive agents for lowering intraocular pressure.

We claim:

1. A compound of Formula I:

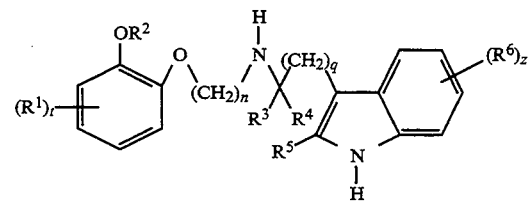

in which
n is 2, 3 or 4;
q is 1, 2 or 3;
t is 0, 1, 2 or 3;
z is 0, 1, 2 or 3; each
$R^1$ and $R^2$ are independently hydroxy, halogen, cyano, ($C_{1-8}$)alkyl, ($C_{1-8}$)alkyloxy or trifluoromethyl;
$R^2$ is fluoro($C_{1-4}$)alkyl, difluoro($C_{1-4}$)alkyl, trifluoro($C_{1-4}$)alkyl, ($C_{1-4}$)alkyloxy($C_{1-4}$)alkyl, oxo($C_{1-4}$)alkyl, ($C_{3-8}$)cycloalkyl, ($C_{3-8}$)cycloalkylmethyl, ally, phenyl($C_{1-4}$)alkyl or heterocyclo($C_{1-8}$)alkyl (wherein the phenyl or heterocyclo is optionally substituted with one to two substituents independently selected from ($C_{1-4}$)alkyl, ($C_{1-4}$)alkyloxy, trifluoromethyl and halogen);
$R^3$ is hydrogen, ($C_{1-4}$)alkyl, ($C_{3-8}$)cycloalkyl, ($C_{3-8}$)cycloalkylmethyl or allyl;

R⁴ is (C₁₋₄)alkyl, (C₃₋₈)cycloalkyl, (C₃₋₈)cycloalkylmethyl or allyl; and

R⁵ is hydrogen, (C₁₋₄)alkyl, (C₃₋₈)cycloalkyl, (C₃₋₈)cycloalkylmethyl, allyl, (C₁₋₄)alkylsulfonyl or aminocarbonyl; or a pharmaceutically acceptable salt, individual isomer or mixture of isomers thereof.

2. The compound of claim 1 in which R³ is (C₁₋₄)alkyl.

3. The compound of claim 2 in which n is 2, q is 1, t is 0, z is 0, R² is cyclopropylmethyl, and R³, R⁴ and R⁵ are each methyl, namely [2-(2-methyl-1H-indol-3-yl)-1,1-dimethylethyl][2-(2-cyclopropylmethyloxyphenoxy)ethyl]amine.

4. The compound of claim 2 in which n is 2, q is 1, t is 0, z is 1, R² is cyclopropylmethyl, R³ and R⁴ are each methyl, R⁵ is hydrogen and R⁶ is chloro at the 5-position, namely [2-(5-chloro-1H-indol-3-yl)-1,1-dimethylethyl][2-(2-cyclopropylmethyloxyphenoxy) ethyl]amine.

5. The compound of claim 2 in which n is 2, q is 1, t is 0, z is 1, R² is cyclopropylmethyl, R³ is methyl, R⁴ and R⁵ are each hydrogen and R⁶ is fluoro at the 6-position, namely [2-(6-fluoro-1H-indol-3-yl)-1-methylethyl][2-(2-cyclopropylmethyloxyphenoxy)amine.

6. A compound of Formula I:

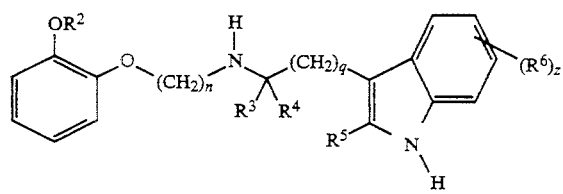

in which n is 2, 3 or 4;

q is 1, 2 or 3;

z is 1, 2 or 3;

R² is hydrogen or (C₁₋₄)alkyl;

R³ is hydrogen, (C₁₋₄)alkyl, (C₃₋₈)cycloalkyl, (C₃₋₈)cycloalkylmethyl or allyl;

R⁴ is (C₁₋₄)alkyl, (C₃₋₈)cycloalkyl, (C₃₋₈)cycloalkylmethyl or allyl;

R⁵ is hydrogen, (C₁₋₄)alkyl, (C₃₋₈)cycloalkyl, (C₃₋₈)cycloalkylmethyl, allyl, (C₁₋₄)alkylsulfonyl or aminocarbonyl; and R⁶ is halogen, cyano or trifluoromethyl; or a pharmaceutically acceptable salt, individual isomer or mixture of isomers thereof.

7. The compound of claim 6 in which n is 2, q is 1, z is 1, R² is 2-methylprop-1-yl, R³, R⁴ and R⁵ are each methyl, and R⁶ is chloro at the 5-position, namely [2-(2-methyl-5-chloro-1H-indol-3-yl)-1,1-dimethylethyl]{2-[2-(2-methylprop-1-yloxy)phenoxy]ethyl}amine.

8. A compound of Formula I:

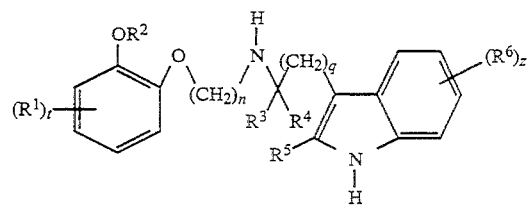

in which n is 2, 3 or 4;

q is 1, 2 or 3;

t is 1, 2 or 3;

z is 0, 1, 2 or 3;

R¹ is hydroxy, halogen, cyano, (C₁₋₈)alkyloxy or trifluoromethyl;

R² is hydrogen or (C₁₋₄)alkyl;

R³ is hydrogen, (C₁₋₄)alkyl, (C₃₋₈)cycloalkyl, (C₃₋₈)cycloalkylmethyl or allyl;

R⁴ is (C₁₋₄)alkyl, (C₃₋₈)cycloalkyl, (C₃₋₈)cycloalkylmethyl or allyl;

R⁵ is hydrogen, (C₁₋₄)alkyl, (C₃₋₈)cycloalkyl, (C₃₋₈)cycloalkylmethyl, allyl, (C₁₋₄)alkylsulfonyl or aminocarbonyl; and R⁶ is hydroxy, halogen, cyano, (C₁₋₈)alkyl, (C₁₋₈)alkyloxy or trifluoromethyl; or a pharmaceutically acceptable salt, individual isomer or mixture of isomers thereof.

9. The compound of claim 8 in which n is 2, q is 1, t is 1, z is 0, R¹ is fluoro at the 5-position, R² is 2-methylprop-1-yl, R³ and R⁴ are each methyl, and R⁵ is hydrogen, namely [2-(1H-indol-3-yl)-1,1-dimethylethyl]{2-[5-fluoro-2-(2-methylprop-1-yloxy)phenoxy]ethyl}amine.

10. A pharmaceutical composition comprising a therapeutically effective amount of a compound of claim 1.

11. A method for treating a condition which can be ameliorated by a drug which blocks α₁-adrenergic receptors in an animal in need of such treatment, which method comprises administering to such an animal a therapeutically effective amount of a compound of claim 1.

12. The method of claim 11 in which the condition is selected from the group consisting anorexia, a cardiovascular disorder, a urinary tract disorder, and increased intraocular pressure.

13. The method of claim 12 in which the condition is a cardiovascular disorder.

14. The method of claim 13 in which the condition is ischemia in vital organs.

15. A method for treating a condition which can be ameliorated by a drug which blocks α₁-adrenergic receptors in an animal in need of such treatment, which method comprises administering to such an animal a therapeutically dfective amount of a compound of claim 6.

16. A method for treating a condition which can be ameliorated by a drug which blocks α₁-adrenergic receptors in an animal in need of such treatment, which method comprises administering to such an animal a therapeutically effective mount of a compound of claim 8.

* * * * *